(12) United States Patent
Chang

(10) Patent No.: US 10,537,509 B2
(45) Date of Patent: Jan. 21, 2020

(54) NAIL GLUE COMPOSITIONS

(71) Applicants: Chin Hao Chang, New Taipei (TW); TriStar Colors, LLC, Duluth, GA (US)

(72) Inventor: Chin Hao Chang, New Taipei (TW)

( * ) Notice: Subject to any disclaimer, the term of this patent is extended or adjusted under 35 U.S.C. 154(b) by 0 days.

(21) Appl. No.: 15/944,649

(22) Filed: Apr. 3, 2018

(65) Prior Publication Data

US 2019/0298628 A1    Oct. 3, 2019

(51) Int. Cl.

| | |
|---|---|
| *A61K 8/40* | (2006.01) |
| *A61K 8/81* | (2006.01) |
| *A61Q 3/02* | (2006.01) |
| *A61K 8/67* | (2006.01) |
| *A61K 33/06* | (2006.01) |
| *A61K 8/64* | (2006.01) |

(52) U.S. Cl.
CPC .................. *A61K 8/40* (2013.01); *A61K 8/64* (2013.01); *A61K 8/8147* (2013.01); *A61K 33/06* (2013.01); *A61Q 3/02* (2013.01); *A61K 8/671* (2013.01); *A61K 8/678* (2013.01)

(58) Field of Classification Search
CPC ........ A61K 8/8152; A61K 8/37; A61K 8/375; A61Q 3/00; A61Q 3/02
See application file for complete search history.

(56) References Cited

U.S. PATENT DOCUMENTS

| | | | |
|---|---|---|---|
| 4,450,848 A | 5/1984 | Ferrigno | |
| 4,704,303 A | 11/1987 | Cornell | |
| 6,060,073 A | 5/2000 | Keller | |
| 6,605,667 B1 * | 8/2003 | Badejo | A61L 24/001 424/443 |
| 2004/0131827 A1 * | 7/2004 | Misiak | C08F 259/06 428/143 |
| 2013/0174981 A1 * | 7/2013 | Kelly | C09J 4/00 156/329 |
| 2014/0329959 A1 * | 11/2014 | Barnes | C09J 4/06 524/553 |

FOREIGN PATENT DOCUMENTS

| | | | | |
|---|---|---|---|---|
| WO | 9700664 | 1/1997 | | |
| WO | WO-2010059230 A1 * | 5/2010 | ....... | A61B 17/00491 |

OTHER PUBLICATIONS

U.S. Appl. No. 16/521,417, filed Jul. 24, 2019, entitled "Nail Polish Composition System and Method of Applying Same".

* cited by examiner

*Primary Examiner* — Mark V Stevens
(74) *Attorney, Agent, or Firm* — Greenberg Traurig, LLP

(57) ABSTRACT

A nail glue composition contains Beta-methoxyethyl cyanoacrylate, octyl cyanoacrylate, and polymethyl methacrylate. The nail glue composition is substantially odorless and has increased softness.

20 Claims, No Drawings

NAIL GLUE COMPOSITIONS

FIELD OF THE INVENTION

The invention relates to nail glue compositions, and, more particularly, to odorless or substantially odorless nail glue compositions.

BACKGROUND OF THE INVENTION

Consumers use nail art to paint, decorate, and enhance their nails cosmetically. One typical nail art technique involves attaching artificial nails to a user's natural nails with the use of a glue or adhesive. While ethyl cyanoacrylate has been used as an adhesive in this nail art technique, this chemical has strong odor, causes brittleness of products and is harmful to the user's health.

SUMMARY OF THE INVENTION

It has been discovered that replacing ethyl cyanoacrylate with octyl cyanoacrylate results in a nail glue composition which is odorless or substantially odorless and has increased softness.

This invention relates to nail glue compositions that contain Beta-methoxyethyl cyanoacrylate, octyl cyanoacrylate, and polymethyl methacrylate. The octyl cyanoacrylate is preferably medical grade octyl cyanoacrylate.

The nail glue compositions preferably contain the following ranges: Beta-methoxyethyl cyanoacrylate is present in the range of about 60 to about 84 wt % of the nail glue composition, octyl cyanoacrylate is present in the range of about 2 to about 40 wt % of the nail glue composition, and polymethyl methacrylate is present in the range of about 0.1 to about 10 wt % of the nail glue composition.

In addition to Beta-methoxyethyl cyanoacrylate, octyl cyanoacrylate and polymethyl methacrylate, the nail glue compositions further comprise one or more additives selected from a group consisting of a vitamin, a protein, calcium gluconate, keratin amino acid and a combination thereof, wherein the one or more additives is present in the range of about 0.01 to about 1 wt % of the nail glue composition.

DETAILED DESCRIPTION OF THE INVENTION

The technical content of invention is described by the following specific embodiments. One of ordinary skill in the art can readily understand the advantages and effects of the present invention upon reading the disclosure of this specification. The present invention may also be practiced or applied with other different implementations. Based on different contexts and applications, the various details in this specification can be modified and changed without departing from the spirit of the disclosure.

It should be noted that terms, such as "first", "second", "one", "a", "an", and the like, are for illustrative purposes only, and are not meant to limit the range implementable by the invention. Any changes or adjustments made to their relative relationships, without modifying the substantial technical contents, are also to be construed as within the range implementable by the invention.

The invention relates to odorless or substantially odorless nail glue compositions which contain octyl cyanoacrylate instead of ethyl cyanoacrylate.

The nail glue compositions of the invention contain Beta-methoxyethyl cyanoacrylate, octyl cyanoacrylate, and polymethyl methacrylate.

Additives such as therapeutic agents, e.g. vitamins, proteins, and/or auxiliaries such as calcium gluconate may be optionally added to the compositions for the further care and protection of the user's nails.

The composition of the invention can be made by combining its components, optionally with stirring. More generally, any known mixing method may be used.

Exemplary compositions according to the invention are provided below, with a listing of the components and their wt % for each exemplary composition.

| Component | CAS # | wt % |
|---|---|---|
| Composition 1 | | |
| Beta-methoxyethyl cyanoacrylate | 027816-23-5 | 84.00 |
| Octyl cyanoacrylate | 133978-15-1 | 10.00 |
| Polymethyl methacrylate | 9011-14-7 | 5.97 |
| Vitamin E | 10191-41-0 | 0.01 |
| Calcium gluconate | 299-28-5 | 0.01 |
| Silk protein | 96690-41-4 | 0.01 |
| TOTAL | | 100.00 |
| Composition 2 | | |
| Beta-methoxyethyl cyanoacrylate | 027816-23-5 | 70.00 |
| Octyl cyanoacrylate | 133978-15-1 | 24.90 |
| Polymethyl methacrylate | 9011-14-7 | 5.97 |
| Vitamin E | 10191-41-0 | 0.01 |
| Vitamin A | 68-26-8 | 0.01 |
| Calcium gluconate | 299-28-5 | 0.01 |
| Silk protein | 96690-41-4 | 0.01 |
| TOTAL | | 100.00 |
| Composition 3 | | |
| Beta-methoxyethyl cyanoacrylate | 027816-23-5 | 60.00 |
| Octyl cyanoacrylate | 133978-15-1 | 35.00 |
| Polymethyl methacrylate | 9011-14-7 | 4.97 |
| Vitamin E | 10191-41-0 | 0.01 |
| Calcium gluconate | 299-28-5 | 0.01 |
| Silk protein | 96690-41-4 | 0.01 |
| TOTAL | | 100.00 |
| Composition 4 | | |
| Beta-methoxyethyl cyanoacrylate | 027816-23-5 | 65.00 |
| Octyl cyanoacrylate | 133978-15-1 | 30.00 |
| Polymethyl methacrylate | 9011-14-7 | 4.96 |
| Vitamin E | 10191-41-0 | 0.01 |
| Calcium gluconate | 299-28-5 | 0.01 |
| Silk protein | 96690-41-4 | 0.01 |
| Keratin Amino Acid | | 0.01 |
| TOTAL | | 100.00 |
| Composition 5 | | |
| Beta-methoxyethyl cyanoacrylate | 027816-23-5 | 72.00 |
| Octyl cyanoacrylate | 133978-15-1 | 23.00 |
| Polymethyl methacrylate | 9011-14-7 | 4.96 |
| Vitamin E | 10191-41-0 | 0.01 |
| Calcium gluconate | 299-28-5 | 0.01 |
| Silk protein | 96690-41-4 | 0.01 |
| Keratin Amino Acid | | 0.01 |
| TOTAL | | 100.00 |

Olfactory Test Methods

Twenty (20) adults (participants) participated in an olfactory test of Composition 1 set out above, and various controls. 30 ml each of Composition 1, tap water, ethyl cyanoacrylate, and bleach (Clorox®) were added to separate microbial culture dishes (diameter of 10 cm, height of 5 cm). Bleach was used because its odor is similar to, but milder than, that of ethyl cyanoacrylate. The microbial culture dishes were placed in a black box with a hole of diameter of 5 cm, allowing the participants to smell the odor through the hole, but not view the culture dishes or the substances therein. The participants assigned, according to their preference, a score of each sample's odor (or lack thereof). The scores ranged from 0 (odorless) to 5 (the strongest odor). The results of the olfactory test are shown in Table 1 below.

TABLE 1

| | Sample | | |
|---|---|---|---|
| | Tap water | Ethyl cyanoacrylate | Composition 1 | Bleach |
| Participant 1 | 0 | 4 | 0 | 1 |
| Participant 2 | 0 | 3 | 0 | 1 |
| Participant 3 | 0 | 5 | 1 | 2 |
| Participant 4 | 0 | 4 | 0 | 1 |
| Participant 5 | 0 | 4 | 1 | 2 |
| Participant 6 | 0 | 3 | 1 | 2 |
| Participant 7 | 0 | 4 | 1 | 3 |
| Participant 8 | 0 | 4 | 0 | 3 |
| Participant 9 | 0 | 4 | 1 | 2 |
| Participant 10 | 0 | 5 | 1 | 3 |
| Participant 11 | 0 | 5 | 0 | 3 |
| Participant 12 | 0 | 4 | 0 | 2 |
| Participant 13 | 0 | 5 | 0 | 2 |
| Participant 14 | 0 | 5 | 0 | 2 |
| Participant 15 | 0 | 5 | 0 | 2 |
| Participant 16 | 0 | 4 | 0 | 2 |
| Participant 17 | 0 | 5 | 1 | 3 |
| Participant 18 | 0 | 5 | 0 | 2 |
| Participant 19 | 0 | 5 | 1 | 2 |
| Participant 20 | 0 | 5 | 1 | 3 |
| Average | 0 | 4.4 | 0.45 | 2.15 |

According to Table 1, there is a very significant difference indicating that Composition 1 has much less odor, compared to a composition containing ethyl cyanoacrylate, or bleach.

Softness Test Methods

Three comparative samples (i.e., controls) and Composition 1 were used to compare the softness of nail glues. The components of the three comparative samples are shown in Table 2 below.

TABLE 2

| Comparative sample 1 | Comparative sample 2 | Comparative sample 3 |
|---|---|---|
| Ethyl Cyanoacrylate 90% | Ethyl Cyanoacrylate 98% | Ethyl Cyanoacrylate 80% |
| Butyl methacrylate 10% | Butyl acrylate 2% | Ethyl Acetate 20% |

The nail glues were made by pouring each of the comparative samples and Composition 1 in a container of size 5 cm×5 cm×0.5 cm for 24 hours, to allow the flake samples to completely dry. The softness of each of the nail glues was determined by their respective torque values. Torque value was measured by using a digital torque meter (model TNP-2, Shimpo Instruments). The flake sample was first twisted by hand until it broke, and the torque value displayed on the digital torque meter was recorded. The higher the torque value of the nail glues, the higher its tolerable torsion was, and the greater the softness of the nail glues. The results of the torque value of the nail glues flake samples under twisting are shown in Table 3 below.

TABLE 3

| Sample | Torque (kg/cm) |
|---|---|
| Composition 1 | 16.5 |
| Comparative sample 1 | 13.2 |
| Comparative sample 2 | 12.5 |
| Comparative sample 3 | 8.7 |

According to Table 3, it can be seen that the softness of the nail glues is greater when it is made from Composition 1, compared to nail glues made from the comparative samples.

Next, each of the nail glues was bent by hand until breaking, with the torque at the breaking point measured and recorded. The results of the torque value of the nail glues under bending are shown in Table 4 below.

TABLE 4

| Sample | Torque (kg/cm) |
|---|---|
| Composition 1 | 0.80 |
| Comparative sample 1 | 0.46 |
| Comparative sample 2 | 0.51 |
| Comparative sample 3 | 0.24 |

The results shown in Table 4 further confirmed that the softness of the nail glues is greater when it is made from Composition 1, compared to nail glues made from the comparative samples.

As seen from the results shown in Tables 1, 3 and 4, the nail glues compositions of the invention are odorless or substantially odorless and have increased softness when compared to compositions that contain ethyl cyanoacrylate.

It should be understood that the embodiments described herein are merely exemplary and that a person skilled in the art may make many variations and modifications without departing from the spirit and scope of the invention. All such variations and modifications are intended to be included within the scope of the invention and the appended claims.

I claim:

1. A nail glue composition comprising: Beta-methoxyethyl cyanoacrylate, 2-octyl cyanoacrylate, polymethyl methacrylate, and a calcium gluconate additive, wherein the nail glue composition is free of ethyl cyanoacrylate.

2. The nail glue composition of claim 1, wherein the 2-octyl cyanoacrylate is medical grade 2-octyl cyanoacrylate.

3. The nail glue composition of claim 1, wherein the Beta-methoxyethyl cyanoacrylate is present in the range of about 60 to about 84 wt % of the nail glue composition.

4. The nail glue composition of claim 1, wherein the 2-octyl cyanoacrylate is present in the range of about 2 to about 40 wt % of the nail glue composition.

5. The nail glue composition of claim 1, wherein the polymethyl methacrylate is present in the range of about 0.1 to about 10 wt % of the nail glue composition.

6. The nail glue composition of claim 1, further comprising a protein additive.

7. The nail glue composition of claim 6, wherein the calcium gluconate and protein additives are present in the range of about 0.01 to about 1 wt % of the nail glue composition.

8. The nail glue composition of claim 7, further comprising a keratin amino acid in the range of 0.01 to 1 wt % of the nail glue composition.

9. The nail glue composition of claim 1, further comprising a vitamin additive selected from a group consisting of Vitamin A, Vitamin E, and a combination thereof.

10. The nail glue composition of claim 9, wherein the vitamin and calcium gluconate additives are present in about equal proportions.

11. A nail glue composition comprising: Beta-methoxyethyl cyanoacrylate, 2-octyl cyanoacrylate, polymethyl methacrylate, and a combination of vitamin, calcium gluconate, and protein additives, wherein the nail glue composition is free of ethyl cyanoacrylate.

12. The nail glue composition of claim 11, further comprising a keratin amino acid additive.

13. The nail glue composition of claim 11, wherein the additives are present in the range of 0.01 to 1 wt % of the nail glue composition.

14. The nail glue composition of claim 11, wherein the protein additive is a silk protein.

15. The nail glue composition of claim 11, wherein the Beta-methoxyethyl cyanoacrylate is present in the range of about 60 to about 84 wt % of the nail glue composition, the 2-octyl cyanoacrylate is present in the range of about 2 to about 40 wt % of the nail glue composition, and the polymethyl methacrylate is present in the range of about 0.1 to about 10 wt % of the nail glue composition.

16. A nail glue composition comprising: Beta-methoxyethyl cyanoacrylate, 2-octyl cyanoacrylate, and polymethyl methacrylate, with a combination of protein and calcium gluconate additives, wherein the nail glue composition is free of ethyl cyanoacrylate.

17. The nail glue composition of claim 16, further comprising a keratin amino acid additive.

18. The nail glue composition of claim 16, wherein the additives are present in the range of 0.01 to 1 wt % of the nail glue composition.

19. The nail glue composition of claim 16, wherein the protein additive is a silk protein.

20. The nail glue composition of claim 16, wherein the Beta-methoxyethyl cyanoacrylate is present in the range of about 60 to about 84 wt % of the nail glue composition, the 2-octyl cyanoacrylate is present in the range of about 2 to about 40 wt % of the nail glue composition, and the polymethyl methacrylate is present in the range of about 0.1 to about 10 wt % of the nail glue composition.

\* \* \* \* \*